(12) United States Patent
Bao et al.

(10) Patent No.: US 9,388,351 B2
(45) Date of Patent: Jul. 12, 2016

(54) FURFURAL TO FUEL

(71) Applicant: PHILLIPS 66 COMPANY, Houston, TX (US)

(72) Inventors: Yun Bao, Sugar Land, TX (US); Kristi A. Fjare, Ponca City, OK (US); Edward L. Sughrue, Edmond, OK (US); TiePan Shi, Bartlesville, OK (US); Brian C. Dunn, Bartlesville, OK (US); Edgar Lotero, Cleveland, OK (US)

(73) Assignee: PHILLIPS 66 COMPANY, Houston, TX (US)

( * ) Notice: Subject to any disclaimer, the term of this patent is extended or adjusted under 35 U.S.C. 154(b) by 0 days.

(21) Appl. No.: 14/740,483

(22) Filed: Jun. 16, 2015

(65) Prior Publication Data

US 2015/0368575 A1 Dec. 24, 2015

Related U.S. Application Data

(60) Provisional application No. 62/013,840, filed on Jun. 18, 2014.

(51) Int. Cl.
| | |
|---|---|
| *C07C 29/141* | (2006.01) |
| *C10L 1/18* | (2006.01) |
| *C07C 29/10* | (2006.01) |
| *C07C 29/17* | (2006.01) |
| *C10L 1/182* | (2006.01) |
| *C07C 29/145* | (2006.01) |

(52) U.S. Cl.
CPC ............. *C10L 1/18* (2013.01); *C07C 29/103* (2013.01); *C07C 29/141* (2013.01); *C07C 29/175* (2013.01); *C07C 29/145* (2013.01); *C10L 1/1824* (2013.01); *C10L 2200/0469* (2013.01); *C10L 2270/023* (2013.01)

(58) Field of Classification Search
CPC .......................... C07C 29/141; C07C 29/145
USPC .................................................. 568/881, 876
See application file for complete search history.

(56) References Cited

U.S. PATENT DOCUMENTS

| | | |
|---|---|---|
| 5,345,756 A | 9/1994 | Jahnke et al. |
| 5,354,344 A | 10/1994 | Takizawa et al. |
| 7,820,867 B2 | 10/2010 | Joensen et al. |
| 2007/0254966 A1 | 11/2007 | Eskin et al. |
| 2008/0228021 A1 | 9/2008 | Joensen et al. |
| 2009/0306415 A1 | 12/2009 | Gruter et al. |
| 2010/0083565 A1 | 4/2010 | Gruter |
| 2011/0000818 A1 | 1/2011 | Xu et al. |

*Primary Examiner* — Elvis O Price
(74) *Attorney, Agent, or Firm* — Phillips 66 Company

(57) ABSTRACT

Furfural is produced through hydrolysis of the hemi-cellulose in corn stover. Furfural may also be produced from other biomass. The direct conversion of furfural to mono-alcohols which can be blended with gasoline is an attractive chemical process for providing biomass into the liquid fuel supply. Examples of such alcohols include 1-butanol, 1-pentanol, 2-pentanol and tetrahydrofurfuryl alcohol. Preferred alcohols include C-4 and C-5 mono-alcohols that have suitable blending properties.

12 Claims, 3 Drawing Sheets

US 9,388,351 B2

FURFURAL TO FUEL

CROSS-REFERENCE TO RELATED APPLICATIONS

This application is a non-provisional application which claims the benefit of and priority to U.S. Provisional Application Ser. No. 62/013,840 filed Jun. 18, 2014, titled "Furfural to Fuel," which is hereby incorporated by reference in its entirety.

STATEMENT REGARDING FEDERALLY SPONSORED RESEARCH OR DEVELOPMENT

None.

FIELD OF THE INVENTION

This invention relates to the production of fuel from biomass and especially to the production of gasoline blending agents from biomass.

BACKGROUND OF THE INVENTION

There is an increasing interest to derive compounds from biomass that may be used as fuel components in gasoline, jet fuel, or diesel fuels. For instance, ethanol is currently produced at large scale as a fuel component for gasoline. Ethanol is presently allowed to be blended into gasoline at a maximum of ten percent of the volume of the resulting gasoline fuel. Higher concentrations of ethanol are likely to cause corrosion issues for vehicles that were not designed for high ethanol fuels such as E85 (eighty-five percent ethanol and fifteen percent hydrocarbon based gasoline). Most gasoline fuel sold in the US includes ethanol.

Biomass may be converted to other materials that are suitable for blending with gasoline fuel, but the cost, efficiency and productivity of systems for producing other blending components have yet to prove satisfactory. Indeed, the US government has been offering renewable energy credits to offset the excess cost of producing such blendstocks. However, the renewable energy credits are designed to diminish over time and there is considerable reluctance to invest in technology that must rely on government support to obtain any profit and even require government support to pay off the cost of the investment. The politics surrounding the production of fuel, even fuels that are envisioned as environmentally beneficial, are uncertain. What is desired is an economical process for converting biomass to fuel or fuel blendstock that profitable without any government or other subsidy.

BRIEF SUMMARY OF THE DISCLOSURE

The invention more particularly relates to a process for converting biomass to fuel comprising biomass is hydrolyzed to a bio crude comprising furfural and at least a portion of the furfural is separated from the bio crude. The separated furfural is then hydrogenated to C4 and C5 mono alcohols which is then useful as renewable gasoline blendstock.

BRIEF DESCRIPTION OF THE DRAWINGS

A more complete understanding of the present invention and benefits thereof may be acquired by referring to the follow description taken in conjunction with the accompanying drawings in which.

DETAILED DESCRIPTION

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

The present invention is related to a new pathway from biomass derived materials to a useful liquid hydrocarbon fuel blendstock. In particular, it has been found that furfural may be directly converted to useful liquid hydrocarbon fuel blending materials if the furfural can be concentrated to substantially eliminate other chemicals that might convert to undesirable products.

Furfural is produced from the hemicellulose in corn stover. Hemicellulose is hydrolyzed under conditions to dehydrate the hemicellulose sugars to furfural. The hemicellulose is separated from the cellulose and lignin prior to the hydrolysis, and the furfural is purified or concentrated by distillation. Furfural may also be obtained from pentose produced by other biomass conversion processes.

The furfural conversion process is a hydrogenation process that includes the addition of hydrogen and is accomplished by catalysts such as Pt, Pd, Ru and combinations thereof. Hydrothermally stable supports such as carbon and titania are preferred. The furfural is diluted with a solvent such as an alcohol or other solvent that is compatible with hydrogenation reaction conditions and catalysts. An interesting solvent is tetrahydrofurfuryl alcohol which is an intermediate to the hydrogenation reaction and is amenable to separation after the hydrogenation step for recycling back to the furfural feedstock. Dilution of the furfural is necessary to minimize the production of coke on the catalyst and other undesirable polymerization reactions.

Figure 1:
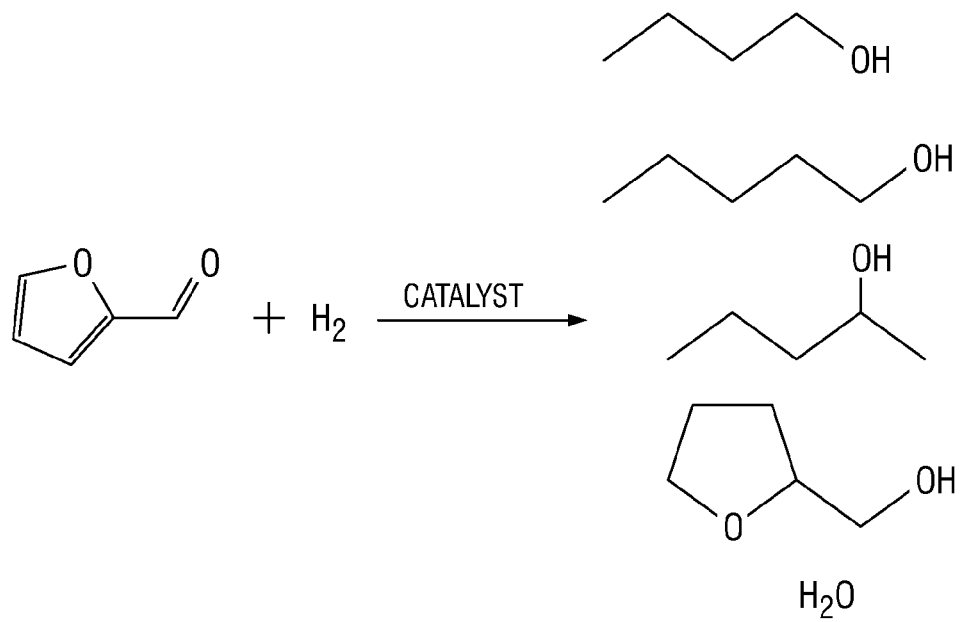
FIG. 1 shows several catalytic reaction paths for reducing furfural to C4 and C5 fuel alcohol products.

Turning to FIG. 1, a chemical reaction is shown with furfural combining with hydrogen over a catalyst to form C4 and C5 mono-alcohols such as 1-butanol, 1-pentanol, 2-pentanol and tetrahydrofurfuryl alcohol. Tetrahydrofurfuryl alcohol is also called hydroxymethyl tetrahydrofuran, but tetrahydrofurfuryl alcohol is the preferred term. The 1-butanol, 1-pentanol and 2-pentanol are already approved for use in gasoline as additives, such as below 16% for butanols and below 15% for pentanols. In the present invention, these known blendstocks are derived from biomass.

Figure 2:
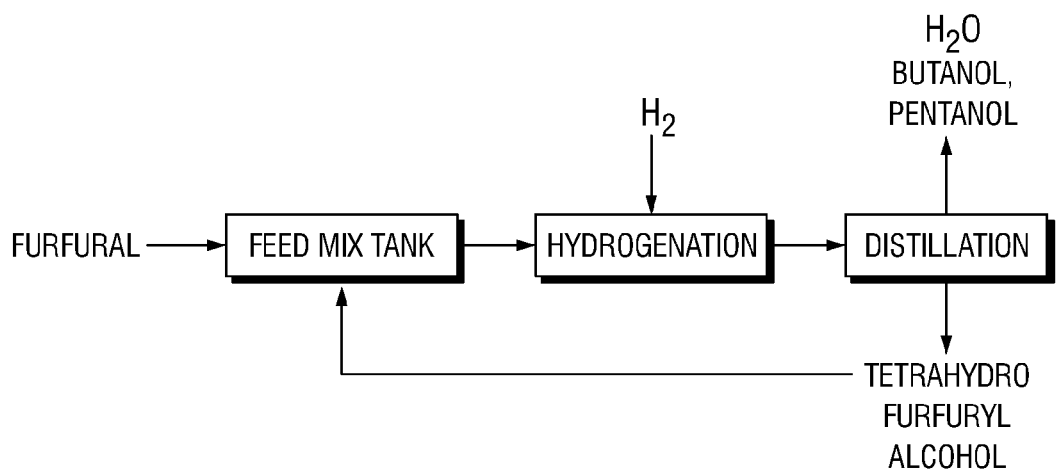
FIG. 2 is a schematic diagram showing a process for making mixed alcohols from furfural.

Turning to FIG. 2, the process is shown in a schematic arrangement 10. Furfural is supplied from a source (not shown) that is concentrated, such as from a distillation column. The furfural is diluted with a mono-alcohol such as tetrahydrofurfuryl alcohol in a mixing tank 12. The diluted furfural solution is then directed to a hydrogenation reactor 15 at a temperature and pressure suitable for the catalytic hydrogenation reaction where the solid hydrogenation catalyst is in a fixed bed and hydrogen is also provided. The products from the hydrogenation reaction are primarily liquid at the reaction conditions and are carried to a simple distillation separator 18 for separation of the tetrahydrofurfuryl alcohol from water and other C4 and C5 mono-alcohols. To the extent that additional tetrahydrofurfuryl alcohol is produced in the hydrogenation process, the tetrahydrofurfuryl alcohol stream 20 may be split to provide the needed diluent or solvent and the remainder may recombined with the C4 and C5 mono-alcohol stream.

As described above, C4 and C5 mono-alcohols may be blended in with gasoline at proportions that meet all the requisite specifications allowed by the US Environmental Protection Agency and the US Federal Trade Commission.

The following examples of certain embodiments of the invention are given. Each example is provided by way of explanation of the invention, one of many embodiments of the invention, and the following examples should not be read to limit, or define, the scope of the invention.

Examples 1-3

Figure 3:
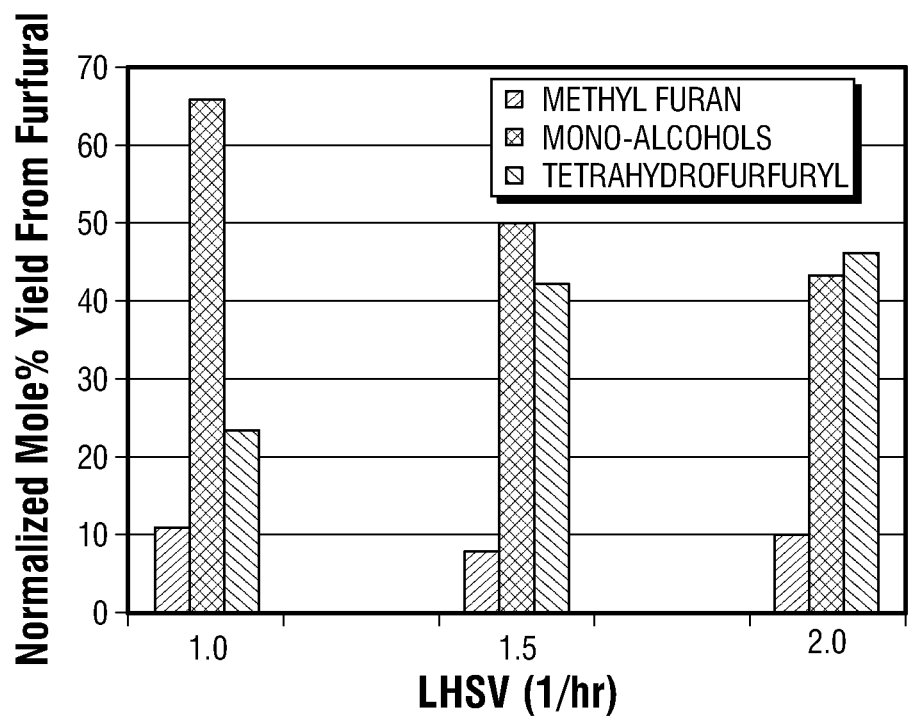
FIG. 3 is a graph the effect of liquid hourly space velocity on alcohol product yield for Examples 1-3.

Hydrogenation of furfural was tested over a 1 wt % $Ru/TiO_2$ catalyst (from Evonik Industries). The feed was 20 vol % furfural and 80 vol % ethanol. Reaction conditions were controlled at 200° C. and 1000 psig with a hydrogen flow of 400 ml/min. The liquid hourly space velocity (LHSV) was varied from 1.0 $h^{-1}$ to 2.0 $h^{-1}$. The furfural was completely converted at the reaction conditions. The major products were mono-alcohols (1-butanol, 1-pentanol, 2-pentanol), tetrahydrofurfuryl alcohol and methyl furan. The normalized mole percentage yields are shown in FIG. 3. Low LHSV favored producing mono-alcohols while higher LHSV favored producing tetrahydrofurfuryl alcohol. The reaction conditions are shown in Table I below and the products are shown in Table II in the middle column.

Examples 4-6

Hydrogenation of furfural was tested over a 1 wt % $Ru/TiO_2$, Ru/C and Ru—Ni/C catalyst generally described as Examples 4, 5 and 6. The feed was 20 vol % furfural and 80 vol % tetrahydrofurfuryl alcohol (TFA). Reaction conditions were controlled at 200° C. and 1000 psig with a hydrogen flow of 400 ml/min. The Liquid Hourly Space Velocity (LHSV) was controlled at 1.0 $h^{-1}$. The furfural was completely converted at the reaction conditions. The product data summary is shown in Tables II, and III below:

TABLE I

| Reaction Conditions. | | | | | | |
|---|---|---|---|---|---|---|
| | Ex 1 | Ex 2 | Ex 3 | Ex 4 | Ex 5 | Ex 6 |
| Furfural Concentration in Alcohol (vol %) | 20 | 20 | 20 | 20 | 35 | 50 |
| Temperature (° C.) | 200 | 200 | 200 | 175 | 200 | 200 |
| Pressure (psig) | 1000 | 1000 | 1000 | 1000 | 1000 | 1000 |
| Hydrogen Flow (mL/min) | 400 | 400 | 400 | 400 | 400 | 400 |
| LHSV (h-1) | 1 | 1.5 | 2 | 1.5 | 1 | 1 |

TABLE II

| Products from hydrogenation | | |
|---|---|---|
| | Ex 1 | Ex 4 |
| Catalyst | Ru/TiO2 | Ru/TiO2 |
| Feed | 20 vol % furfural | 20 vol % furfural |
| | in ethanol | in TFA |
| Furfural Conversion, % | 100 | 100 |
| Carbon Selectivity, %: | | |
| Ethanol | 70.6 | |
| 1-Butanol | 5.4 | 11.0 |
| 1- and 2-Pentanol | 7.5 | 6.3 |
| TFA | 5.1 | 61.7 |
| Methyl THF + THF | 2.3 | 5.2 |
| Unknowns in Liquid Product | 0.5 | 4.5 |
| CH4 | 5.4 | 7.6 |
| C2H6 | 1.3 | 0.3 |
| C3H8 | 0.4 | 0.4 |
| C4H10 + C5H12 | 0.0 | 2.0 |
| CO$x$ | 1.4 | 0.0 |

TABLE III

| Products from hydrogenation | | | |
|---|---|---|---|
| | Ex 4 | Ex 5 | Ex 6 |
| Catalyst | Ru/TiO2 | Ru/C | Ru—Ni/C |
| Furfural conversion, % | 100 | 100 | 99.6 |
| Carbon selectivity, %: | | | |
| 1-Butanol | 11.0 | 1.9 | 0.04 |
| 1- and 2-Pentanol | 6.3 | 3.2 | 0.6 |
| TFA | 61.7 | 80.9 | 86.9 |
| Methyl THF + THF | 5.2 | 5.3 | 7.3 |
| CH4 | 7.6 | 0.8 | 0.02 |
| C2H6—C5H12 | 2.7 | 0.2 | 0 |

TABLE IV

| Products from Hydrogenation Excluding Solvent | | | |
|---|---|---|---|
| | Ex 7 | Ex 8 | Ex 9 |
| | Ru/TiO2 | Ru/C | Ru—Ni/C |
| Furfural conversion, % | 100 | 100 | 99.6 |
| Carbon selectivity, % | | | |
| 1-Butanol | 17 | 17 | 4 |
| 1- and 2-Pentanol | 29 | 10 | 0.3 |
| Methyl THF + THF | 14 | 28 | 58 |
| CH4 | 22 | 4 | 0.1 |
| C2-C5 | 8 | 1 | 0 |
| CO$x$ | 0.01 | 0.06 | 0.1 |
| Unknowns | 11 | 39 | 37 |

Figure 4:
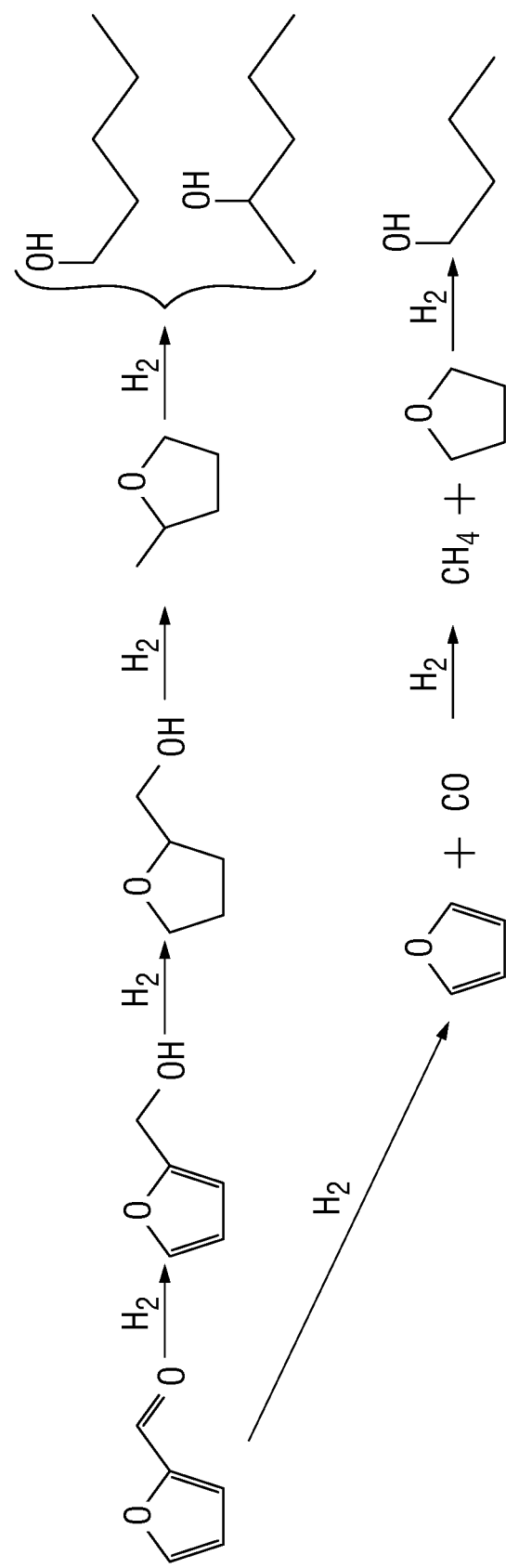
FIG. 4 is a diagram showing the hypothesized chemical pathway for the formation of C4 and C5 alcohol products by furfural reduction.

FIG. 4 shows the likely reaction pathways starting with furfural. Hydrogenation saturates the carbonyl group to form furfuryl alcohol. Further hydrogenation saturates the ring to form tetrahydrofurfuryl alcohol. Higher LHSV seems to leave a higher percentage of the intermediates unreacted. At lower LHSV, the hydroxyl group is separated from the ring, probably by decarbonylation, before the ring is opened to form a C4 mono-alcohol. Carbon monoxide formed by decarbonylation of furfural would be reduced to methane under the reaction conditions.

In closing, it should be noted that the discussion of any reference is not an admission that it is prior art to the present invention, especially any reference that may have a publication date after the priority date of this application. At the same time, each and every claim below is hereby incorporated into this detailed description or specification as an additional embodiment of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:

1. A process for converting biomass to fuel comprising:
 a) hydrolyzing biomass to a bio-crude comprising furfural;
 b) separating at least a portion of the furfural from the bio-crude; and
 c) hydrogenating the separated furfural to C4 and C5 mono-alcohols useful as renewable gasoline blendstock.

2. The process according to claim 1, wherein the step of hydrogenating the separated furfural to C4 and C5 mono-alcohols comprises contacting the separated furfural with a catalyst at catalytically effective conditions.

3. The process according to claim 1, further comprising the step of diluting the furfural prior to hydrogenation with an alcohol.

4. The process according to claim 3, wherein the step of diluting the furfural comprises diluting furfural with ethanol.

5. The process according to claim 3, wherein the step of diluting the furfural comprises diluting furfural with tetrahydrofurfuryl alcohol.

6. The process according to claim 3, wherein the step of diluting the furfural comprises diluting furfural with ethanol or other alcohols.

7. The process according to claim 1, wherein the step of hydrogenating the separated furfural to C4 and C5 mono-alcohols comprises contacting the separated furfural with a precious metal catalyst at a pressure of at least 800 psig and at a temperature of at least 175 C.

8. The process according to claim 7, wherein the precious metal catalyst comprises Ru.

9. The process according to claim 7, wherein the precious metal catalyst comprises Ru—Ni.

10. The process according to claim 7, wherein the catalyst is supported on titania.

11. The process according to claim 7, wherein the catalyst is supported on carbon.

12. The process according to claim 1, wherein the step of hydrogenating the separated furfural to C4 and C5 mono-alcohols further includes producing 1-butanol, 1-pentanol, 2-pentanol and tetrahydrofurfuryl alcohol and wherein the process further comprises separating tetrahydrofurfuryl alcohol from the remaining alcohols and recycling the tetrahydrofurfuryl alcohol for diluting the furfural.

* * * * *